United States Patent
Ottermann et al.

(10) Patent No.: US 12,130,278 B2
(45) Date of Patent: Oct. 29, 2024

(54) LONG-TERM BENDABLE GLASS MATERIAL, AND METHOD FOR THE PRODUCTION OF A LONG-TERM BENDABLE GLASS MATERIAL

(71) Applicant: Schott AG, Mainz (DE)

(72) Inventors: Clemens Ottermann, Hattersheim (DE); Kurt Nattermann, Ockenheim (DE); Markus Heiß-Chouquet, Bischofsheim (DE); Jürgen Vogt, Oberheimbach (DE); Thomas Roßmeier, Bodenheim (DE); Andreas Habeck, Undenheim (DE)

(73) Assignee: Schott AG, Mainz (DE)

( * ) Notice: Subject to any disclaimer, the term of this patent is extended or adjusted under 35 U.S.C. 154(b) by 288 days.

(21) Appl. No.: 17/690,666

(22) Filed: Mar. 9, 2022

(65) Prior Publication Data

US 2022/0194843 A1  Jun. 23, 2022

Related U.S. Application Data

(62) Division of application No. 15/283,933, filed on Oct. 3, 2016, now abandoned.

(30) Foreign Application Priority Data

Oct. 2, 2015  (DE) .................. 10 2015 219 069.2
Sep. 21, 2016  (DE) .................. 10 2016 218 176.9

(51) Int. Cl.

| | |
|---|---|
| G01N 33/38 | (2006.01) |
| B32B 17/10 | (2006.01) |
| B65H 75/08 | (2006.01) |
| C03B 23/00 | (2006.01) |
| C03C 3/085 | (2006.01) |
| C03C 3/091 | (2006.01) |
| C08K 3/40 | (2006.01) |
| G01N 3/20 | (2006.01) |

(52) U.S. Cl.
CPC ........... *G01N 33/386* (2013.01); *B32B 17/10* (2013.01); *B65H 75/08* (2013.01); *C03B 23/0066* (2013.01); *C03C 3/085* (2013.01); *C03C 3/091* (2013.01); *C08K 3/40* (2013.01); *G01N 3/20* (2013.01); *B65H 2701/1842* (2013.01); *G01N 2203/0062* (2013.01)

(58) Field of Classification Search
CPC ................... G01N 33/386; G01N 2203/0062
See application file for complete search history.

(56) References Cited

U.S. PATENT DOCUMENTS

| | | |
|---|---|---|
| 8,241,751 B2 | 8/2012 | Tomamoto et al. |
| 9,321,679 B2 | 4/2016 | Chang et al. |
| 9,908,730 B2 | 3/2018 | Ortner et al. |
| 2002/0070140 A1* | 6/2002 | Okamoto ............... B65D 85/48 |
| | | 206/454 |
| 2011/0177347 A1 | 7/2011 | Tomamoto et al. |
| 2011/0200812 A1 | 8/2011 | Tomamoto et al. |
| 2011/0217521 A1 | 9/2011 | Teranishi et al. |
| 2011/0240499 A1 | 10/2011 | Taniguchi et al. |
| 2012/0135187 A1 | 5/2012 | Takimoto et al. |
| 2013/0045366 A1 | 2/2013 | Merz et al. |
| 2013/0196163 A1 | 8/2013 | Swanson |
| 2013/0240656 A1 | 9/2013 | Merz et al. |
| 2014/0220300 A1* | 8/2014 | Ullmann ............... B32B 17/066 |
| | | 428/141 |
| 2016/0207726 A1* | 7/2016 | Ortner ..................... C03C 3/087 |

FOREIGN PATENT DOCUMENTS

| | | | | |
|---|---|---|---|---|
| TW | 201020183 A | * | 6/2010 | ............. B32B 17/06 |
| TW | 201502505 A | * | 1/2015 | ............... G01N 3/20 |
| WO | 00/66507 | | 11/2000 | |
| WO | 2012/176594 A1 | | 12/2012 | |

OTHER PUBLICATIONS

TW-201502505-A English (Year: 2015).*
TW-201020183-A, English Translation (Year: 2010).*
Chinese Search report dated Apr. 1, 2019 for Chinese Application No. 2016108840529 (2 pages).
"Commodity Science", Xu et al., Tsinghau University Press, 1st edition, Aug. 2011 p. 306 (1 page).
"Glass Technology", Northwest Institute of Light Industry, China Light Industry Press, Aug. 2007, p. 89-92 (5 pages).

* cited by examiner

*Primary Examiner* — Ryan D Walsh
(74) *Attorney, Agent, or Firm* — Taylor IP, P.C.

(57) ABSTRACT

A method for producing long-term bendable glass material includes: bending a glass material in a bending radius in a range of 1 mm to $10^7$ mm; storing the bent glass material for a time period of at least 1 day; inspecting at least a portion of the bent glass material for damage after the storing; and classifying the inspected bent glass material as a reject if damage is detected or as a long-term bendable glass material if no damage is detected.

16 Claims, 4 Drawing Sheets

LONG-TERM BENDABLE GLASS MATERIAL, AND METHOD FOR THE PRODUCTION OF A LONG-TERM BENDABLE GLASS MATERIAL

CROSS-REFERENCE TO RELATED APPLICATIONS

This is a division of U.S. patent application Ser. No. 15/283,933 entitled "LONG-TERM BENDABLE GLASS MATERIAL AND METHOD FOR THE PRODUCTION OF A LONG-TERM BENDABLE GLASS MATERIAL" filed Oct. 3, 2016, which is incorporated in its entirety herein by reference.

BACKGROUND OF THE INVENTION

1. Field of the Invention

The present invention relates to a long-term bendable glass material. The invention also relates to a method for the production of a long-term bendable glass material and its use as a curved glass substrate.

2. Description of the Related Art

Glasses having thicknesses of less than 500 μm—so-called thin glasses—are used in many fields of technology, e.g., displays, screens for optoelectronic components, encapsulations and electric insulating layers.

In order to be able to handle thin glasses in further processing, as well as in storage and transportation, the thin glass ribbon can be wound into a roll. Thus, the glass can be directly unwound from the roll and worked with during subsequent processing. However, one problem hereby is that glass ribbons can be damaged after having been produced; for example, the glass ribbon may have damage along the edges, or cracks. During winding, the glass ribbon is moreover subjected to stresses, such as bending stresses in the glass. These damages and stresses, in particular bending stresses, can result in breakages of the wound glass ribbons. A single breakage can cause considerable problems due to the finishing process having to be interrupted during unwinding of the ribbon at the breakage point. Breaking of the wound glass ribbon can result in situations where damaged glass surfaces that, for example, have cracks in the edge region of the glass ribbon cause crack progression or even breaking to occur. Such a thin glass is, in addition, also used as a curved glass substrate, for example, as a cover glass for a curved display, whereby it is continuously subjected to tensile stress on one side.

It must hereby be ensured that a crack progression that could result in a crack or break is made impossible.

US 2013/0196 163 A1 describes a method for bending of glass, wherein a glass web is laminated onto a reinforcing film so that during bending the neutral plane of the deflection curve is located in the reinforcing film and the glass web in its entirety is located in the deflection-induced compressive stress zone. This requires reinforcing films whose thickness is a multiple of the glass thickness. A slow spreading and thus glass-hard curing adhesive with high strength must be used for the laminate. With the high strength, however, problems can arise if the adhesive cannot easily be removed or removed at all. In any case, the removal of the adhesive represents an additional necessary processing step prior to customization cutting. Moreover, the winding direction is defined. In regard to the breaking strength of the wound glass, the spread of the adhesion and a stress relaxation in the strengthening film must be considered. If, due to the stress relaxation, the neutral plane migrates into the glass web, the glass incurs tensile stress that can even increase during unwinding.

U.S. Pat. No. 8,241,751 describes a glass roll with a low instantaneous likelihood of breakage if a minimum bending radius is adhered to for the curvatures. However, the document does not address the aspect of delayed breaks. In particular, breaks that occur on the edges of the glass ribbon are also ignored. For the dimensioning standards described in the document, glass breakage is to be expected within a very short time period.

WO 2012/176594 A1 suggests that, during transfer of one roll to the next roll, a relative humidity of 40% rF or less should be adhered to in order to avoid a break during the transfer. This should reduce the likelihood of breaks. The method suggested in WO 2012/176 594 A1 shows the best results for relative humidity of ≤1%. The method according to WO 2012/176594 A1, however, only serves the short-term stabilization of the glass ribbon during processing while significantly reducing the humidity. A long-term stabilization improvement of the thin glass in general further processing, or as end product, is not achieved.

A glass element having a thickness of 25 μm to 125 μm has become known from U.S. Pat. No. 9,321,679. From U.S. Pat. No. 9,321,679 it became evident that, with a radius of curvature of 3 mm to 20 mm at 25° C. for at least 60 minutes, no breakage occurs in the glass material. Weibull distributions for verification of the advantages of the etch step are also illustrated in U.S. Pat. No. 9,321,679. Not shown in U.S. Pat. No. 9,321,679 is a proof-test for long-term bendable glass material, or criteria that can be applied to a long-term bendable glass material.

Generally, glass materials having a thickness of ≤500 μm—so-called thin glasses—are not immediately processed further. Rather, the glass material is wound into rolls and stored for a certain period of time. Transportation from storage to an establishment conducting further processing causes additional dynamic loads.

In wound glass rolls, the glass is generally under stress, such as bending stress. In addition, glass ribbons have edge damage or cracks. This can result in the wound glass ribbons breaking, thus rendering further processing impossible. It is therefore desirable to provide a criterion, or proof-test, that permits statements of whether a glass material is long-term bendable. A proof-test is a momentary test and is characterized in that a target value is specified, an actual value is determined, and the actual value is compared to the target value. If, for example, in a proof-test for a long-term bendable glass material the actual value is the crack depth and the crack depth is less than the target value, such as a specified crack depth, then the wound glass material is classified as long-term bendable What is needed in the art is a long-term bendable glass material which can be stored over a long period of time with a very low probability of breaking.

SUMMARY OF THE INVENTION

The present invention provides a long-term bendable glass material as a thin glass, which is stored or used, whereby tensile stress acting over a long time period upon one side and which during further processing of a stored glass roll or during the course of the long-term use has a very low probability of breaking or whereby breakage is avoided.

In addition, a method to produce a long-term bendable glass material, use of a long term-bendable glass material and a proof-test for long-term bendable glass material is provided.

During a proof-test for a long-term bendable glass material, the actual value, namely the crack depth, is compared with a target value, namely the specified crack depth. If the actual value is less than the target value, then a glass material is classified as long-term bendable. With a glass material so classified, the probability of breaking is below 0.1. The crack depth is a measure for the edge stability. The crack depth is thereby a measure for the breaking stress. The critical crack depth for a glass material from which point in time breaking occurs due to tension stress is determined by the following glass parameters: fracture toughness of the glass material, the elasticity modulus of the glass material, the thickness of the glass material and the bending radius of the glass material. The following applies for crack depth $a_c$: $a_c = ((K_{1c} \cdot R)/(E \cdot d))^2$, whereby $K_{1c}$ is the fracture toughness, R is the bending radius, E is the elasticity radius and d is the thickness of the glass material. For current glass materials the fracture toughness is in the range of 0.1 to 1.5 MPa·$\sqrt{m}$. With an elasticity modulus of 75 GPa, a thickness of 100 μm, and a bending radius of 75 mm, a critical or specified crack depth of 49 μm results. According to such a proof-test, every glass roll having a crack depth greater than 49 μm, for example 60 μm, is classified as non-long-term bendable. If the crack depth is less than 49 μm, for example 30 μm, the glass material is categorized as long-term bendable, since then also during storage over a time period of at least 1 day, such as 5 days, 10 days, 50 days, or 300 days, a remaining probability of breaking of less than 0.05, such as 0.01, is achieved for a storage time period of a maximum of at least half a year (6 months), such as one year, 2 years, or a maximum of 5 years.

A glass will generally break as soon as the specified crack depth is exceeded.

According to one aspect of the present invention, a long-term bendable glass material, which can be in the form of a glass material wound onto a roll, such as a glass ribbon having a thickness of less than 500 μm, such as 350 μm, and a minimum thickness of 5 μm, such as 20 μm to 200 μm, is provided whereby the long-term bendable glass material is structured such that the number of breaks N(t) in a bent glass having a bending radius R in the range of 1 mm to $10^7$ mm, such as 5 mm to $10^6$ mm or 10 to $10^3$ mm, developing over the course of time only displays a very low, or no, probability of breaking after a storage period of at least one day, such as at least 3 days, at least 5 days, at least 7 days, at least 10 days, at least 50 days, at least 150 days, or at least 300 days. In the present application, "low probability of breaking or remaining probability of breaking" refers to a probability of breaking t of less than 0.1, such as less than 0.05, or less than 0.01 for a maximum storage period of at least half a year, such as one year, 2 years or 5 years. These probabilities of breaking are attained if the depth of cracks in the glass material do not exceed certain values. The critical crack depth from which breaking occurs is $a_c = ((K_{1c} \cdot R)/(E \cdot d))^2$.

In a proof-test, this critical depth of cracks is the specified depth of cracks (target-value). Surprisingly, it has been demonstrated that a probability of breaking—according to the present invention—of less than 0.1 is achieved, if the depth of cracks is less than previously stated.

Glasses which possess such characteristics distinguish themselves through a very low probability of breaking with long-term bendability, as well as long-term storage in roll form or long-term use as curved substrate.

The glass material can be one having a thickness of less than 500 μm, such as less than 350 μm, and a minimum thickness of 3 μm. The glass thickness can be within the range of 20 μm to 200 μm. Exemplary glass thicknesses are 5, 10, 15, 25, 30, 35, 50, 55, 70, 80, 100, 130, 145, 160, 190, 210 or 280 μm.

If the glass is wound onto a roll, the core diameter of the roll can be greater than 75 mm, such as greater than 100 mm, greater than 150 mm, greater than 300 mm, greater than 400 mm, greater than 500 mm, or greater than 600 mm.

Surprisingly, it has been demonstrated that the glasses formed according to the present invention, such as those in the form of thin glass ribbons or thin glass laminate ribbons that are wound bent onto rolls, are clearly more stable in further processing than curved glasses, which can be in the form of glass rolls that do not achieve the cited probabilities of breaking of less than 0.1 after the specified times. An additional advantage of the present invention is that thin glass ribbons, or thin glass laminate ribbons, that have critical cracks and damage along edges are very easily recognized and can be discarded.

In order to increase the stability of glass rolls, provision can be made to rewind the wound glass rolls after a certain storage time period. Rewinding may, for example, occur in a roll-to-roll process.

Surprisingly, it was noted that glass ribbons displaying the described breaking behavior and which, during the cited storage period of at least one day, such as at least 3 days, at least 5 days, at least 7 days, at least 10 days, at least 50 days, at least 150 days, or at least 300 days have a probability of breaking t of less than 0.1, such as less than 0.05 or less than 0.01 for a maximum storage period of half a year, such as one year, 2 years, and 5 years and possess clear stabilization and higher durability in subsequent processing and further conversion. In particular, they distinguish themselves through long-term bendability. The probability of breaking indicates the probability of a break. 0.1 hereby corresponds to a probability of 10%, 0.05 to a probability of 5%, 0.03 to a probability of 3% and 0.01 to a probability of 1%. The glass ribbons can be wound onto glass rolls.

The consistencies of all samples ensue from a Weibull distribution. The reason for this is the static distribution of the lengths of the micro-cracks, in other words of the crack depth of the micro-cracks. As soon as the underlying distribution is known, a probability of breaking at certain stresses can be specified for each sample. This probability of breaking, however, also depends upon the length of the sample. The longer the sample, the more probable it is that a longer crack occurs. The parameters of a Weibull distribution that were measured by a (destructive) test on one sample set (all samples having the same length $L_0$) are: σ=characteristic breaking stress and m=Weibull modulus. If both these parameters for edge- and surface processing, and the size of the samples with which these parameters were determined, are known, then the probability of breaking $\Phi(\sigma)$ can thus be calculated for a sample with length L that was under tensile stress as: $\Phi(\sigma) = 1 - \exp\{-(L/L_0) \cdot (\sigma/\sigma_0)^m\}$.

With glasses that are subjected to the proof-test, subcritical crack growth occurs during tensile stress. This means that all cracks that reach the critical crack length during the time period of the proof-test will result in a break. The storage is therefore a test with which all micro-cracks that are not shorter than the critical crack length are rejected. Cracks that do not lead to a break within the proof-test, will also not lead to a break subsequently.

Surprisingly, it was demonstrated that with glass material that was classified in the proof-test as being sufficiently stable, an increase in strength occurred. A reason for this is a filleting of the crack tips and thus a resulting increase in strength. As was surprisingly demonstrated, a glass that survived the proof-test can be subjected to considerably greater stress than is applied in the proof-test without the glass breaking, since a strengthening occurs in the glass. The stress to which the glass is subjected may be 5-20% greater than stress determined by the bending radius in the proof-test.

According to one embodiment of the present invention, the wound glass ribbons are placed onto a roll core immediately following production. Subsequently, they are stored, whereby prior to placement onto the roll core, borders—if present—are trimmed from the glass ribbon. The duration of storage of the wound glass ribbons for the proof-test is at least one day and can be a maximum of 60 days, such as 8 days to 30 days.

Storage of the roll according to the present invention can occur at a relative humidity rF in the range of 40% rF to 100% rF, such as 50% rF to 95% rF, 60% rF, or 90% rF. The stored glass rolls can be stored in an enclosed room at temperatures in a range between 10° C. and 30° C., such as 15° C. to 25° C. or 18° C. to 23° C.

As described previously, the long-term bendable glass material can be not only thin glass, but also a thin glass laminate, such a polymer coated thin glass film is described, for example, in WO 00/66507, the disclosure content of which is incorporated into the current application by reference. In the case of the thin glass laminate according to WO 00/66507, a polymer layer consisting of a silicone polymer, a sol-gel polymer, a polycarbonate, a polyethersulfone, a polyacrylate, a polyimide, a cycloolefin-copolymer, a polyarylate or a silicone resin is applied to a thin glass film consisting of aluminosilicate glass, alumino-borosilicate glass or borosilicate glass, such as a non-alkaline borosilicate glass.

Example glass materials that are suitable for the production of glass ribbons having a thickness of less than 500 μm are glasses having the following composition in weight-%:
  $SiO_2$: 40-75;
  $Al_2O_3$: 1-25;
  $B_2O_3$: 0-16;
  alkaline earth oxide: 1-30; and
  alkali oxide: 0-20, such as 0-2.

Generally, all glass compositions are suitable from the aforementioned composition ranges. Exemplary glasses can have a low content of alkali oxides, i.e., an alkali content in a range of 0-2 weight-%, such as glasses AF32, AF37 and AF45 by Schott A G., Mainz.

In one exemplary embodiment, the thin glass is a lithium aluminosilicate glass having the following composition (in weight-%):

| Composition | (Weight-%) |
| --- | --- |
| $SiO_2$ | 55-69 |
| $Al_2O_3$ | 18-25 |
| $Li_2O$ | 3-5 |
| $Na_2O + K_2O$ | 0-30 |
| $MgO + CaO + SrO + BaO$ | 0-5 |
| ZnO | 0-4 |
| $TiO_2$ | 0-5 |
| $ZrO_2$ | 0-5 |
| $TiO_2 + ZrO_2 + SnO_2$ | 2-6 |
| $P_2O_5$ | 0-8 |
| F | 0-1 |
| $B_2O_3$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary lithium aluminosilicate glass of the present invention can consist of the following composition (in weight-%):

| Composition | (Weight-%) |
| --- | --- |
| $SiO_2$ | 57-66 |
| $Al_2O_3$ | 18-23 |
| $Li_2O$ | 3-5 |
| $Na_2O + K_2O$ | 3-25 |
| $MgO + CaO + SrO + BaO$ | 1-4 |
| ZnO | 0-4 |
| $TiO_2$ | 0-4 |
| $ZrO_2$ | 0-5 |
| $TiO_2 + ZrO_2 + SnO_2$ | 2-6 |
| $P_2O_5$ | 0-7 |
| F | 0-1 |
| $B_2O_3$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary lithium aluminosilicate glass of the present invention can consist of the following composition (in weight-%):

| Composition | (Weight-%) |
| --- | --- |
| $SiO_2$ | 57-63 |
| $Al_2O_3$ | 18-22 |
| $Li_2O$ | 3.5-5 |
| $Na_2O + K_2O$ | 5-20 |
| $MgO + CaO + SrO + BaO$ | 0-5 |
| ZnO | 0-3 |
| $TiO_2$ | 0-3 |
| $ZrO_2$ | 0-5 |
| $TiO_2 + ZrO_2 + SnO_2$ | 2-5 |
| $P_2O_5$ | 0-5 |
| F | 0-1 |
| $B_2O_3$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

In one exemplary embodiment, the thin glass is a soda-lime glass having the following composition and contains (in weight-%):

| Composition | (Weight-%) |
| --- | --- |
| $SiO_2$ | 40-81 |
| $Al_2O_3$ | 0-6 |
| $B_2O_3$ | 0-5 |
| $Li_2O + Na_2O + K_2O$ | 5-30 |

-continued

| Composition | (Weight-%) |
|---|---|
| MgO + CaO + SrO + BaO + ZnO | 5-30 |
| $TiO_2$ + $ZrO_2$ | 0-7 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary soda-lime glass of the present invention can consist of the following composition (in weight-%):

| Composition | (Weight-%) |
|---|---|
| $SiO_2$ | 50-81 |
| $Al_2O_3$ | 0-5 |
| $B_2O_3$ | 0-5 |
| $Li_2O$ + $Na_2O$ + $K_2O$ | 5-28 |
| MgO + CaO + SrO + BaO + ZnO | 5-25 |
| $TiO_2$ + $ZrO_2$ | 0-6 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary soda-lime glass of the present invention can consist of the following composition (in weight-%):

| Composition | (Weight-%) |
|---|---|
| $SiO_2$ | 55-76 |
| $Al_2O_3$ | 0-5 |
| $B_2O_3$ | 0-5 |
| $Li_2O$ + $Na_2O$ + $K_2O$ | 5-25 |
| MgO + CaO + SrO + BaO + ZnO | 5-20 |
| $TiO_2$ + $ZrO_2$ | 0-5 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

In one exemplary embodiment, the thin glass is a borosilicate glass having the following composition (in weight-%):

| Composition | (Weight-%) |
|---|---|
| $SiO_2$ | 60-85 |
| $Al_2O_3$ | 0-10 |
| $B_2O_3$ | 5-20 |
| $Li_2O$ + $Na_2O$ + $K_2O$ | 2-16 |
| MgO + CaO + SrO + BaO + ZnO | 0-15 |
| $TiO_2$ + $ZrO_2$ | 0-5 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary borosilicate glass of the present invention can consist of the following composition (in weight-%):

| Composition | (Weight-%) |
|---|---|
| $SiO_2$ | 63-84 |
| $Al_2O_3$ | 0-8 |
| $B_2O_3$ | 5-18 |
| $Li_2O$ + $Na_2O$ + $K_2O$ | 3-14 |
| MgO + CaO + SrO + BaO + ZnO | 0-12 |
| $TiO_2$ + $ZrO_2$ | 0-4 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary borosilicate glass of the present invention can consist of the following composition (in weight-%):

| Composition | (Weight-%) |
|---|---|
| $SiO_2$ | 63-83 |
| $Al_2O_3$ | 0-7 |
| $B_2O_3$ | 5-18 |
| $Li_2O$ + $Na_2O$ + $K_2O$ | 4-14 |
| MgO + CaO + SrO + BaO + ZnO | 0-10 |
| $TiO_2$ + $ZrO_2$ | 0-3 |
| $P_2O_5$ | 0-2 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

In one exemplary embodiment, the thin glass is an alkali metal aluminosilicate glass consisting of the following composition (in weight-%):

| Composition | (Weight-%) |
|---|---|
| $SiO_2$ | 40-75 |
| $Al_2O_3$ | 10-30 |
| $B_2O_3$ | 0-20 |
| $Li_2O$ + $Na_2O$ + $K_2O$ | 4-30 |
| MgO + CaO + SrO + BaO + ZnO | 0-15 |
| $TiO_2$ + $ZrO_2$ | 0-15 |
| $P_2O_5$ | 0-10 |

Potentially, coloring oxides can be added, such as $Nd_2O_3$, $Fe_2O_3$, CoO, NiO, $V_2O_5$, $MnO_2$, $TiO_2$, CuO, $CeO_2$, $Cr_2O_3$; 0-2 weight-% $As_2O_3$, $Sb_2O_3$, $SnO_2$, $SO_3$, Cl, F and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary alkali metal aluminosilicate glass of the present invention can consist of the following composition (in weight-%):

| Composition | (Weight-%) |
|---|---|
| $SiO_2$ | 50-70 |
| $Al_2O_3$ | 10-27 |
| $B_2O_3$ | 0-18 |
| $Li_2O + Na_2O + K_2O$ | 5-28 |
| $MgO + CaO + SrO + BaO + ZnO$ | 0-13 |
| $TiO_2 + ZrO_2$ | 0-13 |
| $P_2O_5$ | 0-9 |

Potentially, coloring oxides can be added, such as $Nd_2O_3$, $Fe_2O_3$, $CoO$, $NiO$, $V_2O_5$, $MnO_2$, $TiO_2$, $CuO$, $CeO_2$, $Cr_2O_3$; 0-2 weight-% $As_2O_3$, $Sb_2O_3$, $SnO_2$, $SO_3$, $Cl$, $F$ and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary alkali metal aluminosilicate glass of the present invention can consist of the following composition (in weight-%):

| Composition | (Weight-%) |
|---|---|
| $SiO_2$ | 55-68 |
| $Al_2O_3$ | 10-27 |
| $B_2O_3$ | 0-15 |
| $Li_2O + Na_2O + K_2O$ | 4-27 |
| $MgO + CaO + SrO + BaO + ZnO$ | 0-12 |
| $TiO_2 + ZrO_2$ | 0-10 |
| $P_2O_5$ | 0-8 |

Potentially, coloring oxides can be added, such as $Nd_2O_3$, $Fe_2O_3$, $CoO$, $NiO$, $V_2O_5$, $MnO_2$, $TiO_2$, $CuO$, $CeO_2$, $Cr_2O_3$; 0-2 weight-% $As_2O_3$, $Sb_2O_3$, $SnO_2$, $SO_3$, $Cl$, $F$ and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

In one exemplary embodiment, the thin glass is an aluminosilicate glass with low alkali content and consisting of the following composition (in weight-%):

| Composition | (Weight-%) |
|---|---|
| $SiO_2$ | 50-75 |
| $Al_2O_3$ | 7-25 |
| $B_2O_3$ | 0-20 |
| $Li_2O + Na_2O + K_2O$ | 0-4 |
| $MgO + CaO + SrO + BaO + ZnO$ | 5-25 |
| $TiO_2 + ZrO_2$ | 0-10 |
| $P_2O_5$ | 0-5 |

Potentially, coloring oxides can be added, such as $Nd_2O_3$, $Fe_2O_3$, $CoO$, $NiO$, $V_2O_5$, $MnO_2$, $TiO_2$, $CuO$, $CeO_2$, $Cr_2O_3$; 0-2 weight-% $As_2O_3$, $Sb_2O_3$, $SnO_2$, $SO_3$, $Cl$, $F$ and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary aluminosilicate glass with low alkali content of the present invention can consist of the following composition (in weight-%):

| Composition | (Weight-%) |
|---|---|
| $SiO_2$ | 52-73 |
| $Al_2O_3$ | 7-23 |
| $B_2O_3$ | 0-18 |
| $Li_2O + Na_2O + K_2O$ | 0-4 |
| $MgO + CaO + SrO + BaO + ZnO$ | 5-23 |
| $TiO_2 + ZrO_2$ | 0-10 |
| $P_2O_5$ | 0-5 |

Potentially, coloring oxides can be added, such as $Nd_2O_3$, $Fe_2O_3$, $CoO$, $NiO$, $V_2O_5$, $MnO_2$, $TiO_2$, $CuO$, $CeO_2$, $Cr_2O_3$; 0-2 weight-% $As_2O_3$, $Sb_2O_3$, $SnO_2$, $SO_3$, $Cl$, $F$ and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

Another exemplary aluminosilicate glass with low alkali content of the present invention can consist of the following composition (in weight-%):

| Composition | (Weight-%) |
|---|---|
| $SiO_2$ | 53-71 |
| $Al_2O_3$ | 7-22 |
| $B_2O_3$ | 0-18 |
| $Li_2O + Na_2O + K_2O$ | 0-4 |
| $MgO + CaO + SrO + BaO + ZnO$ | 5-22 |
| $TiO_2 + ZrO_2$ | 0-8 |
| $P_2O_5$ | 0-5 |

Potentially, coloring oxides can be added, such as $Nd_2O_3$, $Fe_2O_3$, $CoO$, $NiO$, $V_2O_5$, $MnO_2$, $TiO_2$, $CuO$, $CeO_2$, $Cr_2O_3$; 0-2 weight-% $As_2O_3$, $Sb_2O_3$, $SnO_2$, $SO_3$, $Cl$, $F$ and/or $CeO_2$ can be added as a refining agent; and 0-5 weight-% rare earth oxides can also be added in order to introduce magnetic, photon- or optical functions into the glass layer or plate. The total volume of the total composition is 100 weight-%.

The glass material can be a thin glass or glass film having a thickness of less than 500 µm, such as less than 350 µm and a minimum thickness of 3 µm. The thickness can be in the range of 20 µm to 200 µm. Exemplary glass film thicknesses are 5, 10, 15, 25, 30, 35, 50, 55, 70, 80, 100, 130, 145, 160, 190, 210 or 280 µm.

By rewinding the glass ribbons and changing the direction of curvature after a quarter or half of the total storage period, the stability can be further increased. The glass is hereby rewound in a roll-to-roll process.

The bent glass, such as wound glass, is subjected to a moderate tensile stress $\sigma_{app}$ that is less than the following mathematical term:

$$1.15 \cdot \text{Min}\left(\overline{\sigma}_a - \Delta_a 0.4 \cdot \left(1 - \ln\left(\frac{A_{ref}}{A_{App}}\Phi\right)\right), \overline{\sigma}_e - \Delta_e 0.4 \cdot \left(1 - \ln\left(\frac{L_{ref}}{L_{App}}\Phi\right)\right)\right)$$

whereby $\overline{\sigma}_a$ and $\overline{\sigma}_e$ are average values of the tensile stress on breakages of thin glass samples that are subjected to bending stresses, whereby $L_{ref}$ describes the edge length and $A_{ref}$ describes the surface of the samples, whereby $\overline{\sigma}_a$ is the average value of the tensile stress in the surface of the sample during breaking, and $\overline{\sigma}_e$ is the average value of the tensile stress on a break originating from the edge of the sample, and whereby $\Delta_e$ and $\Delta_a$ are the standard deviations of the average values $\overline{\sigma}_e$ or respectively $\overline{\sigma}_a$, and whereby $A_{app}$ is the surface of the thin glass and $L_{app}$ the added edge lengths of opposite edges of the thin glass material and a predetermined maximum breakage quota within a time period of at least half a year.

The bent glasses, which can be glasses that are wound into rolls, such as thin glasses having a thickness of less than 500 μm, such as less than 350 μm. The minimum thickness can be 3 μm. An exemplary thickness range is between 20 μm and 200 μm. Exemplary glass film thicknesses are 5, 10, 15, 25, 30, 35, 50, 55, 70, 80, 100, 130, 145, 160, 190, 210 or 280 μm.

The information in regard to the maximum tensile stress for the bent glasses, such as glass rolls, is based on the recognition that breaks along the edges and in the surface of the glass trace back to various defects in the glass, and that the probabilities of breakage are statistically independent of each other. Thus, glass strengths in regard to break resistance along the edges and in the surface are considered independent of each other.

The actual break resistance is calculated according to the above mathematical term through the minimum of the tensile stresses on breaks in the surface and along the edges. In this way, the typically different life spans of the thin glasses are also considered in regard to breaks along the edges and on surfaces that occur during bending. When specifying a life span, the maximum probability of breakage Φ can be 0.1 or less (in other words 10% max.), such as less than 0.05 (less than 5%) or less than 0.03 (less than 3%) when storing long-term in a rolled state, or in a bent state, or during utilization in bent state.

A low probability of breaking in specified storage conditions is noted with mostly alkali-free borosilicate glasses. Such exemplary borosilicate glasses have a composition including the following components in weight-% on oxide basis:

$SiO_2$: 40-75;
$Al_2O_3$: 1-25;
$B_2O_3$: 0-16;
alkaline earth oxide: 1-30; and
alkali oxide: 0-1.

Other exemplary glasses have a composition including the following components in weight-% on oxide basis:

$SiO_2$: 45-70;
$Al_2O_3$: 5-25;
$B_2O_3$: 1-16;
alkaline earth oxide: 1-30; and
alkali oxide: 0-1.

In addition to the bendable long-term storable and usable glass materials, the present invention also provides a method for the production of a long-term bendable glass material, which can be in the form of a glass material that is wound onto a roll, such as a glass ribbon having a thickness of less than 500 μm, such as less than 350 μm, and a minimum thickness of 3 μm, such as in the range of 20 μm to 200 μm. The method includes the following steps: the glass material is initially bent in a bending radius R in the range of 1 mm to $10^7$ mm, such as 5 mm to $10^6$ mm or 10 to $10^3$ mm. The bent glass material is stored for a time period of at least 1 day, such as at least 3 days, at least 5 days, at least 7 days, at least 10 days, at least 50 days, at least 150 days, or at least 300 days; after storage over a time period of at least 1 day, such as at least 3 days, to at most 500 days, such as at least 50 days to at most 300 days, the bent glass material is inspected for cracks, breaks, tears, fracture points, and defects, and the bent glass material or a cut-off of the bent glass material is classified as reject with a defect marking if damage such as cracks, breaks, tears, fracture points, and defects has been detected, or the bent glass material is classified as a long-term bendable glass material if damage has not been detected.

In order to increase the stability of the glass ribbons, provision can be made to rewind the glass roll one time or several times. This can occur in a roll-to-roll process.

"Reject" is also to be understood that damaged sections such as those with cracks, breaks, tears, fracture points, and defects are marked and are rejected or removed in a later step.

The marking can occur on the glass ribbon with the assistance of a defect marking that is placed, for example, on a defect point $F_i$ at a location $(x_i, y_i)$ on the glass ribbon.

The placement of defect markings has made it possible that entire sections of the glass ribbons no longer have to be removed as rejects. Rather, the placement of a defect marking $F_i$ has enabled processors of a glass roll to identify the section of the glass ribbon with the defect and thus to not utilize it in the manufacture of products which—due to the defect—cannot be produced according to specification. For example, the defect markings can be read and considered during processing of the glass roll or the glass ribbon when unwinding the glass roll, such as when unraveling the endless ribbon. Accordingly, a further damage inspection can be foregone during further processing. In addition, reject rates can be reduced. Waste due to contaminations of the glass ribbon that are erroneously classified as defect points can be avoided since the defect inspection occurs earlier, such as immediately following drawing of the glass ribbon from the melt and prior to winding or laminating of the glass ribbon. If the layers of the glass ribbon are separated by removable separation layers that are connected with the glass ribbon, the defect marking can also be placed on the separation layer. If the glass ribbon also comprises a metal layer or plastic layer that is connected with the glass layer, the defect marking may also be placed on the metal layer or plastic layer. The previously described classified or categorized glass materials are characterized by a long-term bendability whereby practically no damage occurs during the storage period or utilization in bent state, in other words under tensile stress on one glass material side.

In the bent condition, long-term bendable glass materials can have bending radii R in the range of 1 mm to $10^7$ mm, such as 5 mm to $10^6$ mm or 10 to $10^3$ mm.

The glass material can have a thickness of less than 500 μm, such as less than 350 μm, and a minimum thickness of 3 μm, such as within the range of 20 μm to 200 μm. Exemplary glass thicknesses are 5, 10, 15, 25, 30, 35, 50, 55, 70, 80, 100, 130, 145, 160, 190, 210 or 280 μm. If a long-term bendable glass material is wound onto a roll, the core diameter of the roll can be greater than 75 mm, such as greater than 100 mm, greater than 150 mm, greater than 300 mm, greater than 400 mm, greater than 500 mm, or greater than 600 mm.

Storage of the roll according to the present invention can occur at a relative humidity rF in the range of 40% rF to 100% rF, such as 50% rF to 95% rF or between 60% rF and 90% rF. The roll can be subjected to a temperature between 10° C. and 30° C., such as between 15° C. and 25° C. or in between 18° C. and 23° C. and to standard atmospheric conditions. Storage in a humid environment, as opposed to dry storage, allows for healing of the cracks to possibly occur. Generally, it would be expected that the glasses that are stored infinitely would break. However, this is countered by a healing of the cracks due to aging of the glass. Storage in a humid environment is conducive to healing of cracks, since healing of cracks is achieved by a rapid filleting of the cracks. Generally, it has turned out that the more humid the storage, the more rapid the filleting of the cracks. Filleting of cracks ensures that no more cracks originate and that the cracks can no longer spread. In addition, the strength of the glass or glass ribbon is increased.

The effect of the aging of the glass is at 0-40%, such as 5% or 5-20% of the strength increase over time.

In the process of producing a glass with low probability of breaking, rewinding of the glass material or a conversion into sheets from the stored roll and/or inspection of the roll for breaks in the glass occurs after storage, whereby screening occurs of wound glass or respectively wound roll, with detection of defects.

The glass material can be a thin glass or a glass film having a thickness of less than 500 µm, such as less than 350 µm. The minimum thickness can be 3 µm. An exemplary thickness range is between 20 µm and 200 µm. Exemplary glass film thicknesses are 5, 10, 15, 25, 30, 35, 50, 55, 70, 80, 100, 130, 145, 160, 190, 210 or 280 µm.

Regarding the different glass materials, exemplary glass materials are previously described herein. Exemplary glasses can have a low content of alkali oxides, i.e., have an alkali content in a range of 0-2 weight-%, such as glasses AF32, AF37 and AF45 by Schott A G., Mainz.

The present invention moreover provides the use of a glass material—that, according to the present invention, is classified as long-term bendable glass material—as a bent glass substrate, such as one having a bending radius of 1 to $10^7$ mm, such as 5 to $10^6$ mm or 10 to $10^3$ mm. The long-term bendable glass materials are initially wound onto a glass roll and are stored for an extended period of time. Subsequently, glass segments are unwound from the roll and are subjected to a permanent tensile stress. This causes bending of the glass to a curved glass substrate having the previously cited bending radii. The curved glass substrate may be used, for example, in a curved display as a cover glass or as glass on a touch panel. Rewinding is also possible.

The present invention also provides a proof-test or test method for characterization of a long-term bendable glass material. The proof-test includes storage of a glass material, which can be in the form of a wound glass material, such as a glass ribbon having a thickness of less than 500 µm or less than 350 µm and a minimum thickness of 3 µm or within the range of 20 µm to 200 µm for a storage period of at least 1 day, such as at least 3 days, at least 5 days, at least 7 days, at least 10 days, at least 50 days, at least 150 days, or at least 300 days. After the storage time, a crack depth in the glass ribbon is determined and compared with a predefined crack depth. If the crack depth is less than the predefined crack depth, then the glass material is determined to be a long-term bendable glass material, so that the probability of breaking t is less than 0.05, such as less than 0.01, for a maximum storage period of half a year, such as one year, 2 years and a maximum of 5 years.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
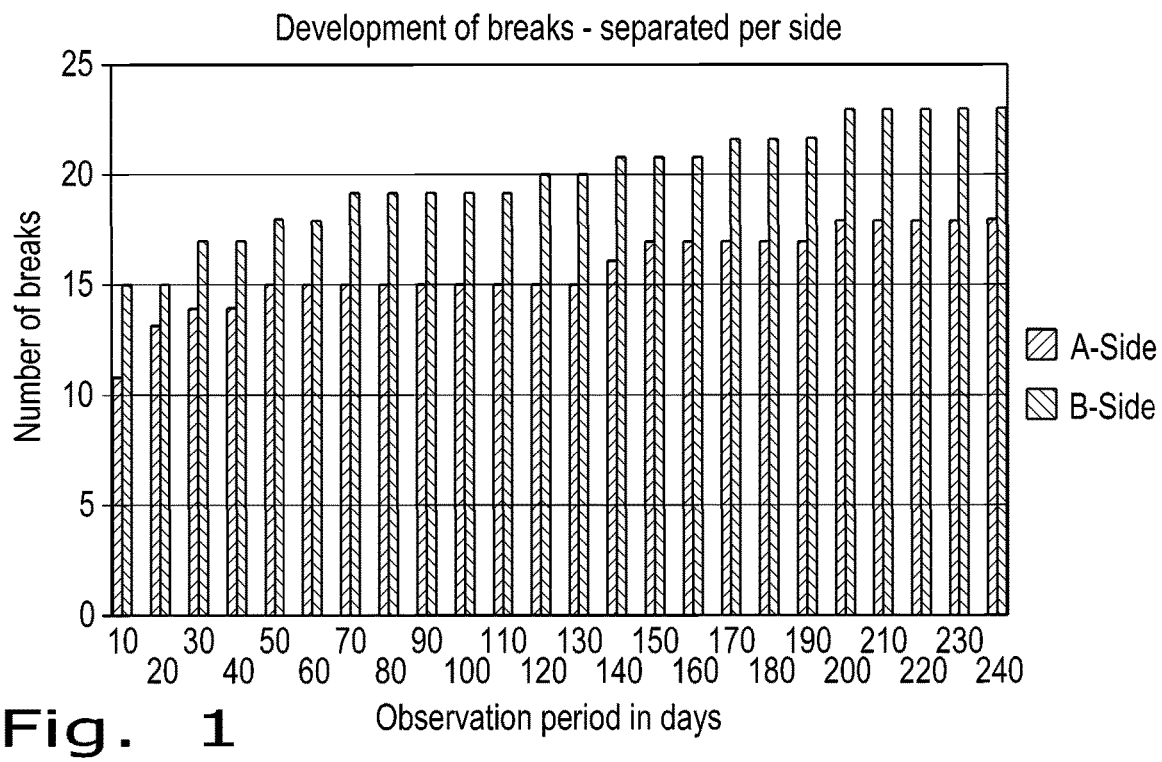
FIG. 1 is a progression of a break development for a 50 µm thick thin glass film of glass AF32.
Figure 2:
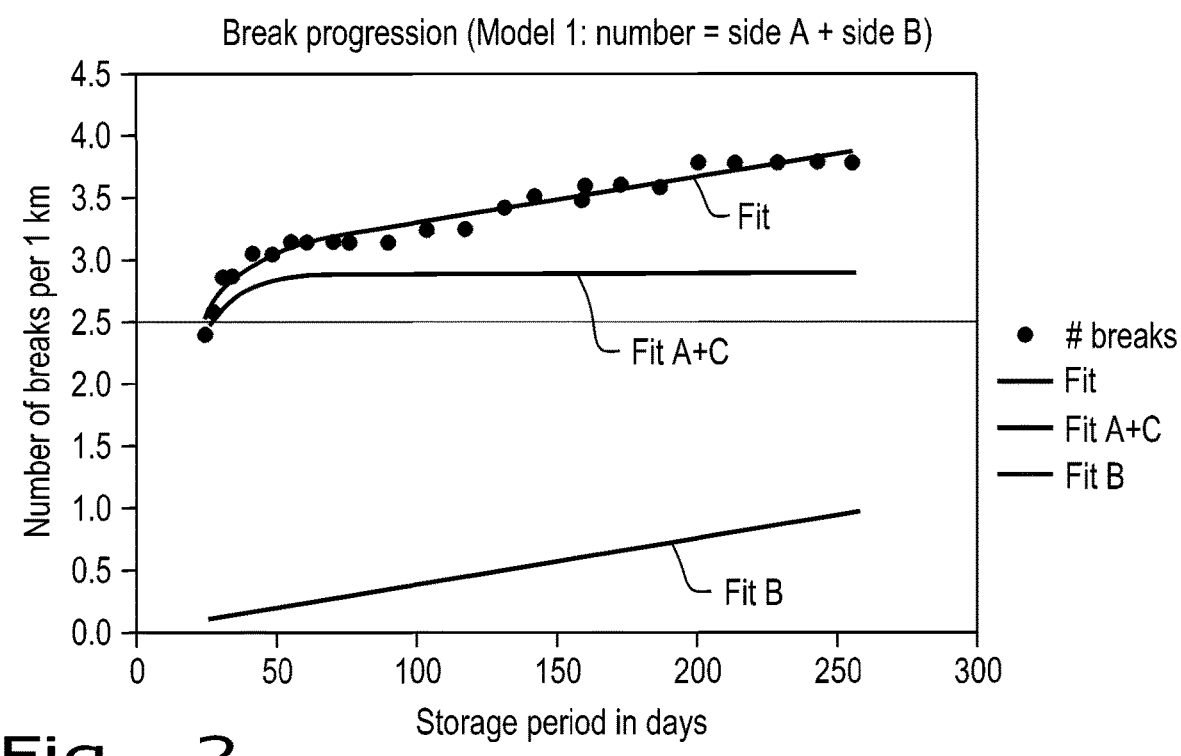
FIG. 2 is break progression for a 100 µm thick thin glass film of glass AF32.

Referring now to the drawings, and more particularly to FIGS. 1 and 2, the probability of breakage is given over time for a multitude of glass rolls having a diameter of 85 mm, including a glass roll having a thickness of 50 µm. Intermediate layers consisting of a physically crosslinked, closed-cell polyolefin-foam, as offered under the trade name Alveolit by SEKISUI ALVEO BS GmbH/D-Bad Sobernheim is inserted between the individual glass layers. The glass rolls are enclosed in plastic covers and are stored at room temperature. The moisture was hereby variable between 20% and 85%. Overall, several observations were conducted. The total observation period was 300 days. The development of a break in a 50 µm thick thin glass film of AF32 is illustrated in FIG. 1. As can be seen, the probability of breaking strongly increases initially and remains then on a largely constant level. At best, a small increase can be detected after a certain storage time.

Rolls of thin glass ribbons with a thickness of 50 µm consisting of an alkali-free alumino-borosilicate glass were inspected as glass material. This glass AF32 by Schott A G., Mainz is a glass consisting of the following components in weight-%:

$SiO_2$: 61.4;
$Al_2O_3$: 17.5;
$B_2O_3$: 10.5;
alkaline earth oxide: 10.3; and
alkali oxide: 0.

As can be seen in FIG. 1, the number of breaks strongly increases at the beginning to 4 breaks/km length of film and increases only slowly with extended storage times. After 4 weeks or 30 days, a virtually stationary state is reached and no significant increase in the number of breaks is detected. The probability of breaks after 30 days is less than 0.03, such as less than 0.01. Over several months of storage period, the glass film shows no significant increase in the number of breaks The following applies to the tension σ in the glass roll:

$$\sigma = E \cdot \frac{t}{2R}$$

E=the Young's (elastic) modulus which, in the case of AF32 is 74 GPa;

t=the glass thickness which, in the case of AF32 is 50 μm; and the core diameter R of the roll=85 mm.

For the tension σ for the roll consisting of a 50 μm thick AF32 glass film this suggests a value of approximately 21 MPa for the tension in the glass roll; for a 100 μm thick glass film a tension of 45 MPa.

FIG. 2 illustrates the results for a 100 μm thick AF32 glass film. As can be seen from FIG. 2, the number of breaks also increases rapidly in this case within 25 days. In contrast to the 50 μm thick glass film, the level from which the number of breaks remains largely constant is reached only after more than 100 days. As in the case with the 50 μm thick glass film, the probability of breaking when stored longer than 150 days is 0.01, in other words 1% lower. For the tension in the glass roll, a value of σ=45 MPa is determined.

The glass rolls that are stored over at least 1 day, such as at least 5 days, at least 7 days, at least 10 days, at least 50 days, at least 150 days, or at least 300 days with low probability of breaking are categorized as remaining stable over a long-term storage period, or long-term bendable, or usable in a curved state. Such glasses find use in curved indicator devices, such as curved cover glasses or display glasses.

Surprisingly, after conducting the proof-test, i.e., classifying the glass material as long-term bendable, an increase in strength was achieved due to filleting of the crack tips.

With glass that is subjected to the proof-test, subcritical crack formation occurs due to tensile stress. This means that all cracks that reach the critical crack length, i.e., the predetermined crack length during a given time period, will result in a break. Storage in accordance with the proof-test is therefore a test during which glasses with micro-cracks that are not shorter than the critical crack length—that is the target value—are rejected. Cracks that do not lead to a break within the first short time period, will also not lead to a break after a long time period.

This makes it possible to put a greater load onto the glass roll after conducting the proof-test. It has been shown that loads can be greater of up to 20% than in the proof-test. The range of the possible load increase is therefore 0 to 20%. Values of 5%, 10%, 15% load increase are possible. As is the case in the proof-test, the load is adjusted through the winding radius. The following applies for the tensile stress:

$$\sigma = E \cdot \frac{t}{2R}$$

whereby:

t: is the thickness of the glass material;

R: is the winding radius; and

E: is the Young's modulus.

FIGS. 3-10 demonstrate the surprising fact that the glass becomes stronger during storage.

Figure 3:
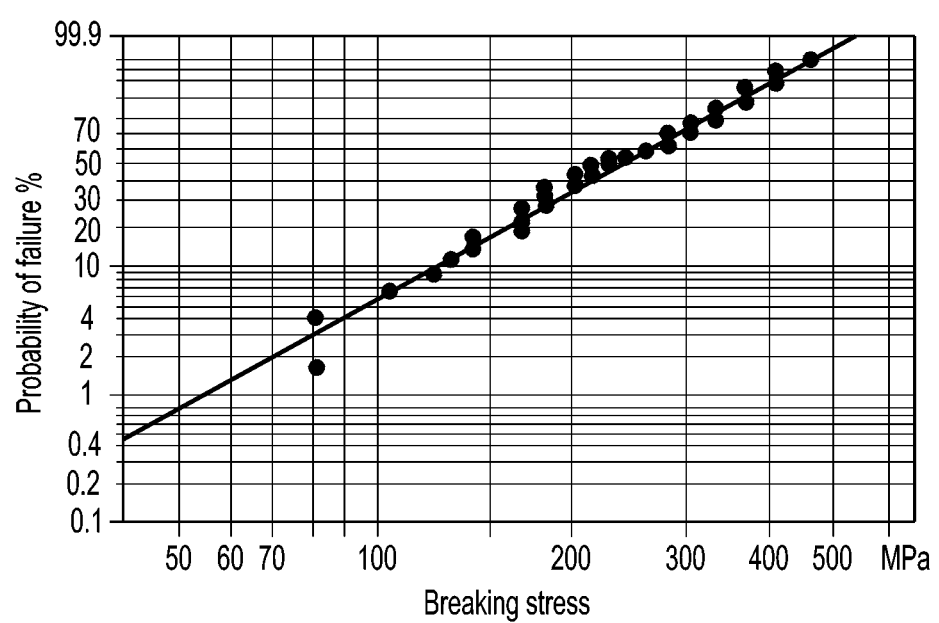
FIG. 3 is a Weibull-diagram of strength (breaking stress) over the probability of failure of a reference glass sample.

FIG. 3 illustrates the Weibull diagram as strengths of a reference sample.

Figure 4:
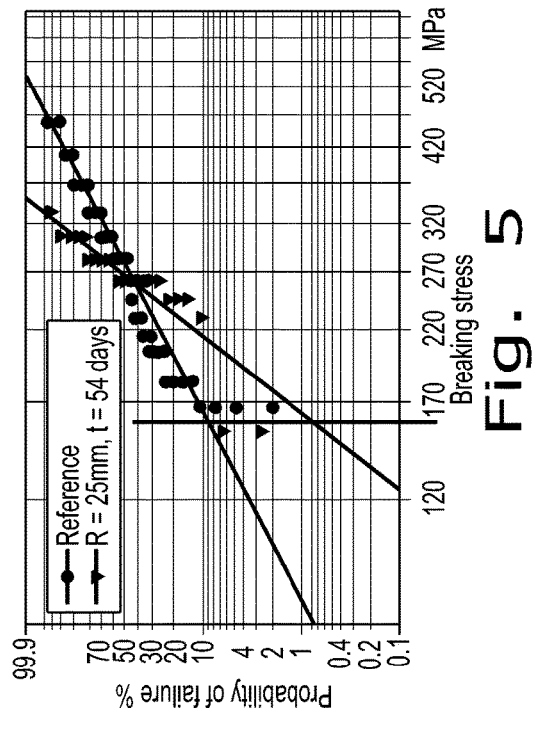
FIG. 4 is a Weibull-diagram of strength (breaking stress) over the probability of failure for a glass sample with a radius of 30 mm.
Figure 5:
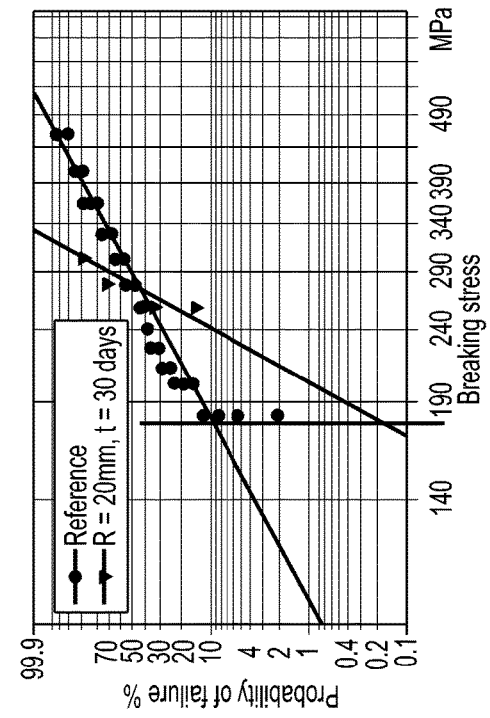
FIG. 5 is a Weibull-diagram of strength (breaking stress) over the probability of failure for a glass sample with a radius of 25 mm.
Figure 6:
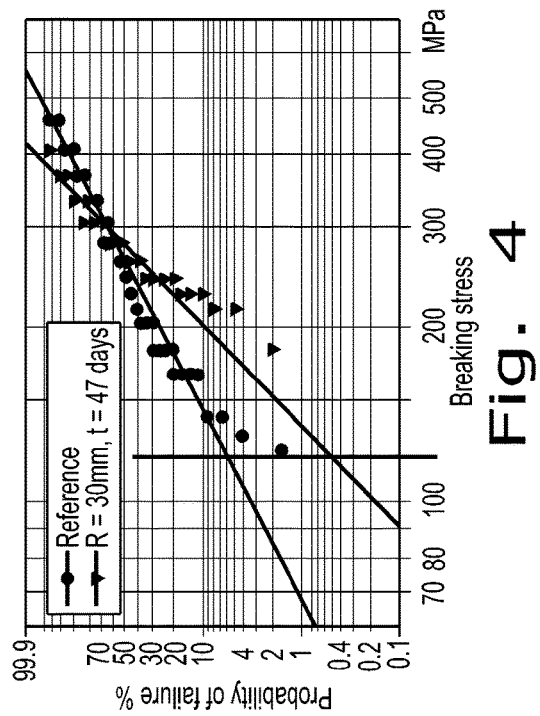
FIG. 6 is a Weibull-diagram of strength (breaking stress) over the probability of failure for a glass sample with a radius of 22.5 mm.
Figure 7:
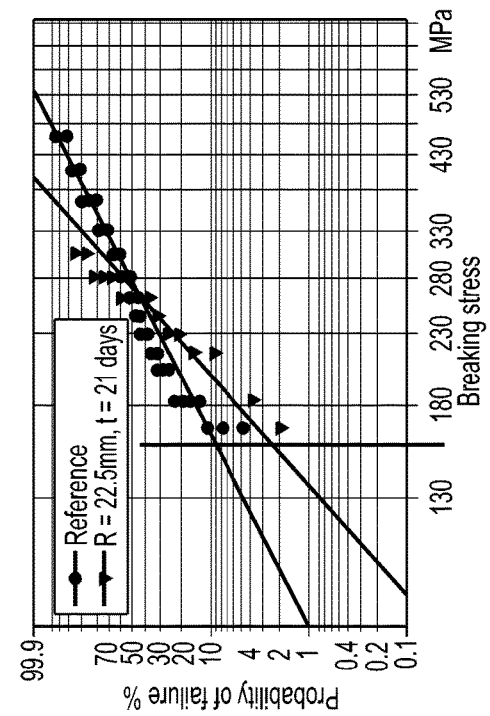
FIG. 7 is a Weibull-diagram of strength (breaking stress) over the probability of failure for a glass sample with a radius of 20 mm.
Figure 9:
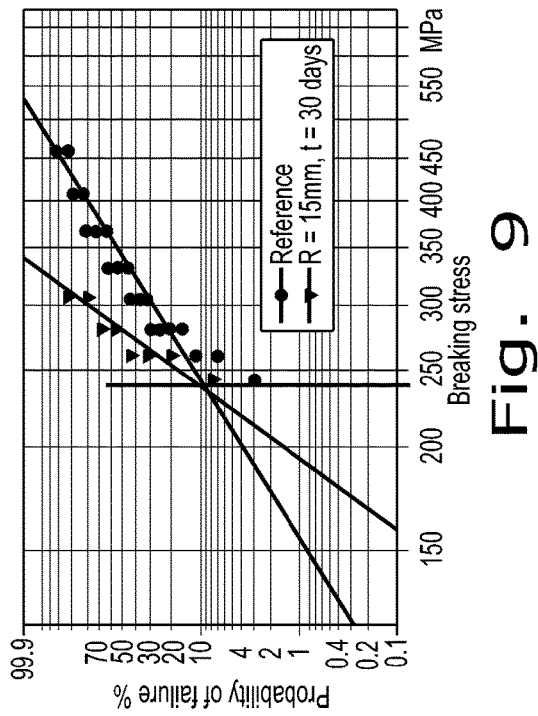
FIG. 9 is a Weibull-diagram of strength (breaking stress) over the probability of failure for a glass sample with a radius of 15 mm.
Figure 8:
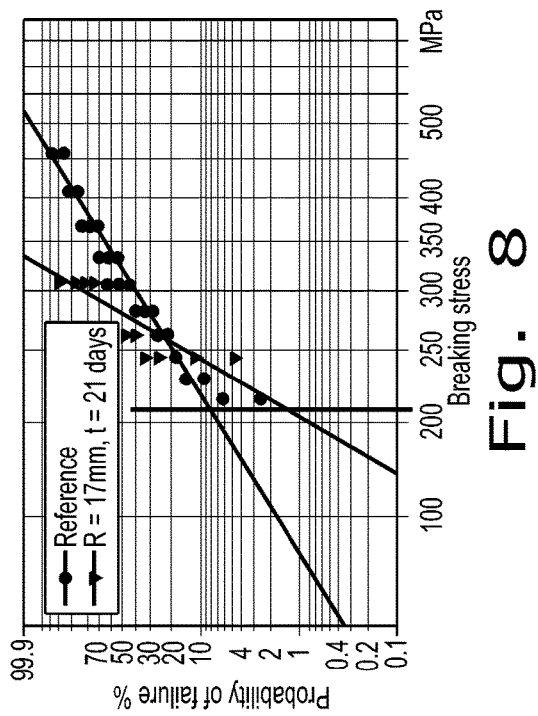
FIG. 8 is a Weibull-diagram of strength (breaking stress) over the probability of failure for a glass sample with a radius of 17 mm.
Figure 10:
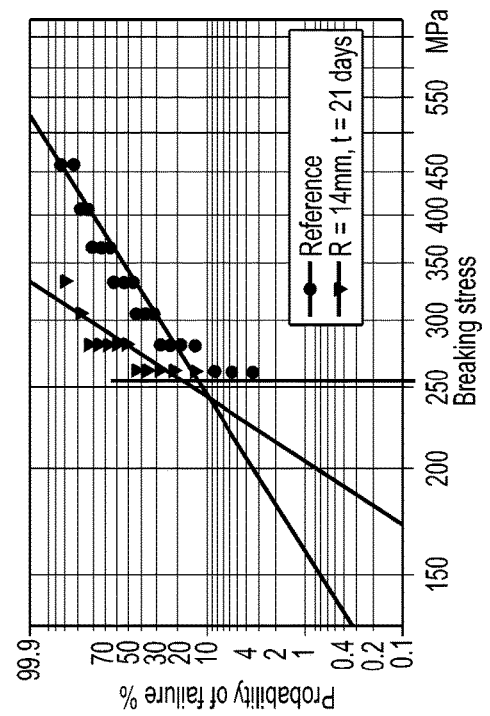
FIG. 10 is a Weibull-diagram of strength (breaking stress) over the probability of failure for a glass sample with a radius of 14 mm.

FIGS. 4-10 illustrate the Weibull diagrams of glasses that were stored longer, after conducting the proof-test and under greater loads than during the proof-test as a comparison to a reference sample from FIG. 3. In FIG. 4, the inspected sample had a radius of 30 mm; in FIG. 5, the inspected sample had a radius of 25 mm; in FIG. 6, the inspected sample had a radius of 22.5 mm; in FIG. 7, the inspected sample had a radius of 20 mm; in FIG. 8, the inspected sample had a radius of 17 mm; in FIG. 9, the inspected sample had a radius of 15 mm; and in FIG. 10, the inspected sample had a radius of 14 mm. The glasses are maintained over a longer time period under strong tension after the proof-test was conducted.

Surprisingly, it can be appreciated from FIGS. 4-10 that the samples with high strengths become clearly worse, but the samples whose original strength is not much above the load limit are clearly better. However, if the stresses become too great, the effect is no longer easily recognizable.

With the present invention, it has been recognized for the first time how one can proceed in order to facilitate a long-term bendability for glass on a roll or in a curved application. Moreover, a proof-test is provided with which it is possible to classify long-term bendable glass samples.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for producing long-term bendable glass material, comprising:
bending a glass material in a bending radius in a range of 1 mm to $10^7$ mm; winding said glass material onto a roll, said glass material having a maximum thickness of 500 μm and a minimum thickness of 3 μm; storing said bent glass material for a time period of at least 1 day; inspecting at least a portion of said bent glass material for damage after said storing; and classifying said inspected bent glass material as a reject if damage is detected or as a long-term bendable glass material if no damage is detected.

2. The method according to claim 1, further comprising rewinding said wound glass material from said roll onto a second roll.

3. The method according to claim 1, wherein said glass material comprises the following components in weight-%:

| | |
|---|---|
| $SiO_2$ | 40-75; |
| $Al_2O_3$ | 1-25; |
| $B_2O_3$ | 0-16; |
| alkaline earth oxide | 0-30; and |
| alkali oxide | 0-20. |

4. The method according to claim 1, wherein said inspected glass material is a cut-off of said bent glass material.

5. The method according to claim 1, wherein said glass material comprises at least one coating.

6. The method according to claim 1, further comprising pre-treating said glass material prior to said bending.

7. The method according to claim 1, wherein said glass material is a composite material having a polymer film.

8. The method according to claim 1, wherein said glass material is stored at least one of at a relative humidity in a range between 40% and 100% and at a temperature in a range between 10° C. and 30° C.

9. The method according to claim 1, wherein said damage is a crack in said glass material having a crack depth greater than $((K_{1c} \cdot R)/(E \cdot d))^2$, wherein $K_{1c}$ is a fracture toughness of said glass material, R is a bending radius of said glass material, E is an elasticity modulus of said glass material, and d is a thickness of said glass material.

10. A method for proof testing glass material, comprising:
bending a glass material;
storing said bent glass material for a period of at least 1 day;
determining a crack is present in the bent glass material;
determining a crack depth of the crack in said glass material after said storing;
comparing said determined crack depth with a predefined crack depth; and
classifying said glass material as a long-term bendable glass material if said crack depth is less than said predetermined crack depth such that a remaining probability of breaking is less than 0.1 for a maximum storage period of half a year.

11. The method according to claim 10, further comprising defining said predetermined crack depth as $((K_{1c} \cdot R)/(E \cdot d))^2$, wherein $K_{1c}$ is a fracture toughness of said glass material, R is a bending radius of said glass material, E is an elasticity modulus of said glass material, and d is a thickness of said glass material.

12. The method according to claim 11, wherein at least one of said fracture toughness is in a range of 0.1 to 1.5 MPa·$\sqrt{m}$, said elasticity modulus is in a range of 40 to 150 GPa, and said bending radius is in a range of 1 mm to $10^7$ mm.

13. The method according to claim 10, wherein said glass material comprises the following components in weight-%:

| | |
|---|---|
| $SiO_2$ | 40-75; |
| $Al_2O_3$ | 1-25; |
| $B_2O_3$ | 0-30; and |
| alkali oxide | 0-20. |

14. The method according to claim 10, wherein said glass material comprises at least one coating.

15. The method according to claim 10, further comprising pre-treating said glass material prior to said bending.

16. The method according to claim 10, wherein said glass material is a composite material having a polymer film.

* * * * *